United States Patent [19]
Aidam et al.

[11] Patent Number: 5,764,354
[45] Date of Patent: Jun. 9, 1998

[54] TWO-BEAM GAS ANALYZER AND METHOD FOR CALIBRATING A TWO-BEAM GAS ANALYZER

[75] Inventors: Eckhard Aidam, Jockgrim; Johann Weinel, Karlsruhe, both of Germany

[73] Assignee: Siemens Aktiengesellschaft, Munich, Germany

[21] Appl. No.: 772,201

[22] Filed: Dec. 20, 1996

[30] Foreign Application Priority Data

Dec. 20, 1995 [DE] Germany ................ 195 47 787.1

[51] Int. Cl.$^6$ .................... G01J 1/02; G01N 21/00
[52] U.S. Cl. .................... 356/243; 356/435; 356/437; 250/343
[58] Field of Search .............. 356/243, 432, 356/433, 436, 437, 438; 250/343, 345, 344

[56] References Cited

U.S. PATENT DOCUMENTS

| | | | |
|---|---|---|---|
| 3,072,787 | 1/1963 | Moyat | 250/343 |
| 3,560,736 | 2/1971 | Billetdeaux | 250/343 |
| 4,101,221 | 7/1978 | Schunck et al. | 356/205 |
| 4,682,031 | 7/1987 | Fabinski et al. | 250/343 |
| 4,694,174 | 9/1987 | Erath | 250/343 |
| 4,794,255 | 12/1988 | Miyatake et al. | 250/345 |
| 5,468,962 | 11/1995 | Ohishi et al. | 250/343 |

FOREIGN PATENT DOCUMENTS

| | | |
|---|---|---|
| 0 199 365 | 10/1986 | European Pat. Off. . |
| 26 14 181 | 10/1977 | Germany . |
| 41 11 187 | 8/1992 | Germany . |

OTHER PUBLICATIONS

Staab, J., Industrielle Gasanalyse (Industrial gas analysis), Oct. 1993, Technisches Messen 60 (1993) 11, pp. 444–449.
Staab, J., Industrielle Gasanalyse (Industrial gas analysis), Jul. 8, 1993 Technisches Messen 60 (1993) 10, pp. 398–401.
Staab, J., Industrielle Gasanalyse (Industrial gas analysis), Jul. 8, 1991, Technisches Messen 58 (1991) 11, pp. 452–457.
Staab, J., Industrielle Gasanalyse (Industrial gas analysis), Nov. 1991, Technisches Messen 58 (1991) 12, PP. 490–494.

*Primary Examiner*—Hoa Q. Pham
*Attorney, Agent, or Firm*—Kenyon & Kenyon

[57] ABSTRACT

In a two-beam gas analyzer, a measurement beam passes through a measurement cuvette filled with a measurement gas, and a comparison beam passes through a comparison cuvette filled with a comparison gas. Using a detector arrangement, a difference signal is generated from the beams exiting from the two cuvettes resulting in a measurement value which corresponds to the measurement gas concentration when weighted with a weighting factor. To allow recalibration after a calibration of the two-beam gas analyzer with calibration gas and adjustment of the weighting factor to a value which results in the appropriate calibration value as the measurement value, without having to fill the measurement cuvette with a calibration gas, an additional factor is determined when the measurement cuvette is not filled or is filled with inert gas. Thus, the difference signal corresponds to the calibration value when weighted with the weighting factor and the additional factor. During subsequent calibration processes, a zero point deviation of the difference signal is determined when the measurement cuvette is not filled or is filled with inert gas, and the weighting factor is corrected when the comparison beam is also interrupted in such a way that the difference signal corresponds to the calibration value when weighted with the corrected weighting factor and the additional factor.

11 Claims, 3 Drawing Sheets

| 100 | 100 |
|---|---|
| -30% | 0 |
| 70 | 100 |
| 30 ||

FIG. 2

| 100 | 100 |
|---|---|
| 0 | 0 |
| 100 | 0 |
| 100 ||

FIG. 3

| 100 | 100 |
|---|---|
| -20% | 0 |
| 80 | 100 |
| 20 ||

FIG. 4

| 111,11 | 88,89 |
|---|---|
| -20% | 0 |
| 88,89 | 88,89 |
| 0 ||

FIG. 5

| 111,11 | 88,89 |
|---|---|
| -20% | 0 |
| 88,89 | 0 |
| 88,89 ||

FIG. 6

| 111,11 | 88,89 |
|---|---|
| -20% -40% | 0 |
| 53,33 | 88,89 |
| 35,56 ||

FIG. 7

| 100 | 100 |
|---|---|
| -20% | 0 |
| 80 | 0 |
| 80 ||

FIG. 8

| 100 | 100 |
|---|---|
| -20% -40% | 0 |
| 48 | 100 |
| 52 ||

FIG. 9 ced in the input of a signal processing device 18, which generates a measurement value corresponding to the measurement gas concentration, by weighting the difference signal with a weighting factor.

TWO-BEAM GAS ANALYZER AND METHOD FOR CALIBRATING A TWO-BEAM GAS ANALYZER

FIELD OF THE INVENTION

The present invention relates to a two-beam gas analyzer and to a method for calibrating a two-beam gas analyzer.

BACKGROUND INFORMATION

European Patent Application No. 0 199 365 describes an infrared two-beam gas analyzer in which the infrared radiation emitted from a radiation source is divided into a pulsing measurement beam and a pulsing comparison beam using a beam splitter followed by a light chopper. The measurement beam passes through a measurement cuvette filled with measurement gas, where an intensity attenuation specific to the measurement gas takes place, while the comparison beam passes through a comparison cuvette filled with a comparison gas, preferably a non-absorbent inert gas. Each cuvette is followed by a gas-filled receiver chamber, in which the radiation exiting from the cuvette in each instance generates pressure variations by means of absorption. Because of the prior absorption by the measurement gas in the measurement cuvette, the pressure variations caused in the receiver chambers are different. The resulting pressure difference is determined by means of a pressure or flow detector arranged in a connection between the two receiver chambers, with a measurement value being generated by weighting a difference signal obtained.

The weighting factor for generating the measurement value can be determined in that the measurement cuvette is filled with a calibration gas with a known absorption behavior, with the weighting factor being adjusted in such a way that a measurement value which corresponds to the calibration value of the calibration gas is obtained.

Entrainment of dirt into the measurement cuvette by the measurement gas, changes in the radiation source, or other interference influences make it necessary to regularly recalibrate the two-beam gas analyzer. This can be done with a calibration gas in each instance, as described above, but this is complicated in view of the gas equipment required.

There is the possibility of duplicating the intensity attenuation by the calibration gas using a changeable diaphragm in the measurement beam path. In that case, however, non-uniform contaminations in the measurement cuvette which are covered by the diaphragm, for example, on the walls of the measurement cuvette, are not taken into consideration in the recalibration. Furthermore, the accuracy of the diaphragm adjustment must lie in the magnitude range of the interference influence of the contamination as part of the entire intensity of the measurement beam, i.e., in the per mille range according to empirical data. This can only be achieved, however, with a great deal of effort and equipment expense.

Another possibility of avoiding filling the measurement cuvette with calibration gas during recalibration is to push a calibration cuvette with calibration gas sealed in it into the measurement beam path, instead of the measurement cuvette. However, the design effort for the special calibration cuvette and the necessary shifting or pivoting mechanism is very high. In addition, the intervention in the measurement beam path is problematic, since even small changes in the position of the measurement cuvette have an interference influence on the measurement system when the cuvette is pushed back into the measurement beam path.

SUMMARY OF THE INVENTION

The present invention discloses a two-beam gas analyzer and an accurate and simple method of recalibrating same without having to fill the measurement cuvette with a calibration gas. The two-beam analyzer includes a measurement cuvette which can be filled with a measurement gas and through which a measurement beam is passed, a comparison cuvette which is filled with a comparison gas and through which a comparison beam is passed, a detector arrangement which follows the measurement cuvette and the comparison cuvette, which generates a difference signal from the beams which exit each of the two cuvettes, and a signal processing device which generates a measurement value corresponding to the measurement gas concentration, by weighting the difference signal with a weighting factor which is adjusted, when the measurement cuvette is filled with calibration gas, so that the measurement value corresponds to the calibration value of the calibration gas.

In accordance with the present invention, when the measurement cuvette is not filled, or is filled with an inert gas, and the comparison beam is interrupted, an additional factor is determined in such a manner that the difference signal corresponds to the calibration value when weighted with the weighting factor and the additional factor. During subsequent calibration processes when the measurement cuvette is not filled, or is filled with an inert gas, a zero point deviation of the difference signal is determined, and when the comparison beam is interrupted, the weighting factor is corrected in such a manner that the difference signal corresponds to the calibration value when weighted with the corrected weighting factor and the additional factor.

BRIEF DESCRIPTION OF THE DRAWINGS

FIGS. 2 through 9 show a schematic representations of the two-beam gas analyzer, with numerical examples to illustrate the calibration and measurement processes of the present invention.

DETAILED DESCRIPTION

Figure 1:
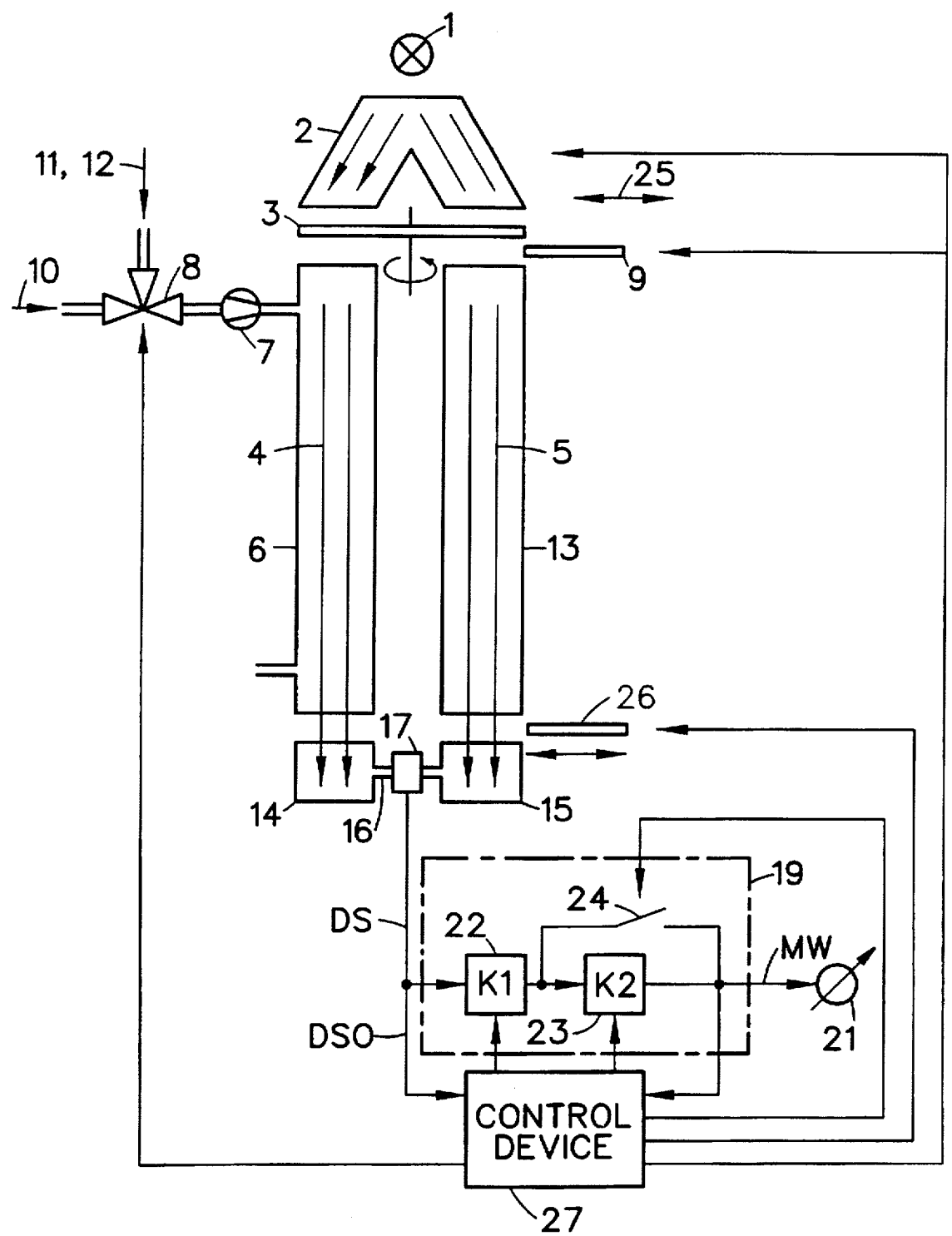
FIG. 1 shows an exemplary embodiment of a two-beam gas analyzer according to the present invention.

FIG. 1 shows a two-beam gas analyzer with an infrared radiation source 1. The radiation from source 1 is divided into a pulsing measurement beam 4 and a pulsing comparison beam 5 using a beam splitter 2 followed by a light chopper 3 comprised of a rotating diaphragm wheel. A measurement cuvette 6 is arranged in the path of the measurement beam 4. The measurement cuvette 6 can be optionally filled with a measurement gas 10 to be analyzed, or with an inert gas 11 which does not absorb the radiation, or for calibration, with a calibration gas 12. Depending on the type and concentration of the gas contained therein, a pre-absorption of the measurement beam 4 takes place in the measurement cuvette 6. A comparison cuvette 13 lies in the beam path of the comparison beam 5, in which a comparison gas, e.g. an inert gas, is sealed. Both the measurement cuvette 6 and the comparison cuvette 13 are each followed by a corresponding gas-filled receiver chamber 14 or 15 to receive the radiation which exits from the cuvette 6 or 13, respectively.

The pulsing radiation received generates pressure variations in the receiver chambers 14 and 15, respectively, by means of absorption, where these pressure variations can be different depending on the prior absorption in the measurement cuvette 6. Both receiver chambers 14 and 15 are connected with one another via a connecting line 16, in which a pressure or flow detector 17 to detect the pressure differences between the two receiver chambers 14 and 15, i.e., the gas flows caused as a result, is arranged. A difference signal DS obtained is weighted in a signal processing device 19, so that a measurement value MW is obtained at its output, which is displayed or recorded in a display or recording device 21. In operational analysis of measurement gas 10, weighting of the difference signal DS takes place in a device 22, shown as an amplifier stage, with a weighting factor K1 previously determined in a calibration process. A second device 23, located in the signal path, e.g. a second amplifier stage, with a signal-weighting additional factor K2, is bridged by means of a controllable switching device 24.

To calibrate the two-beam gas analyzer, a balanced introduction of radiation into the measurement cuvette 6 and the comparison cuvette 13 can be adjusted by mechanically moving the radiation source 1 or the beam splitter 2 along the double arrow 25, or by inserting a movable beam-limiting element 9 into the comparison beam path. Accordingly, a larger portion of the radiation enters the measurement cuvette 4 and a smaller portion of the radiation enters the comparison cuvette 13. For example, if the movable beam-limiting element 9 is moved to the left, the portion of the beam passing into the comparison cuvette 13 is reduced. Furthermore, the comparison beam 5 can be interrupted by a controllable diaphragm 26, where the diaphragm 26 can also be arranged between the beam splitter 2 and the comparison cuvette 13, in contrast to the representation in FIG. 1. The corresponding control for adjusting of the diaphragm 26, the beam coupling into the measurement cuvette 6 and the comparison cuvette 13 is provided using a control device 27, which also controls the valves 8 as well as the switching device 24 and the adjustment of the weighting factor K1 and the additional factor K2.

For a first-time calibration of the two-beam gas analyzer, in other words for determining the weighting factor K1, the measurement cuvette 6 has a calibration gas flowing through it. The calibration value of the calibration gas, i.e. the correct measurement value MW to be displayed, is known. With the amplifier stage 23 bridged, by closing the switch 24, the weighting factor K1 is adjusted by the control 27 in such a way that the measurement value MW corresponds to the predetermined calibration value.

In FIG. 2, the calibration process according to the present invention is illustrated using a simple numerical example, in which a beam with an intensity value of 100 is introduced both into the measurement cuvette 6 and the comparison cuvette 13, by means of the arrangement of the radiation source 1 and the beam splitter 2. The intensity attenuation caused by the calibration gas in the measurement cuvette 6 is 30%, while the inert gas in the comparison cuvette 13 does not cause any intensity attenuation. The intensity values received in the two receiver chambers 14 and 15 are therefore 70 and 100, respectively, which results in the value of 30 for the difference signal DS. This corresponds to the calibration value of the calibration gas, so that the weighting factor is set at K1=1.

For subsequent recalibration processes, which are to take place without calibration gas, the measurement cuvette 6 is filled with an inert gas after the first-time calibration, and the beam path of the comparison beam 5 to the receiver chamber 15 is completely interrupted using the diaphragm 26. With the switch 24 open, the additional factor K2 is now adjusted in such a way that the measurement value MW corresponds to the calibration value again. As FIG. 3 shows, proceeding from the numerical example of FIG. 2, the intensity value 100 is received in the receiver chamber 14, and the intensity value 0 is received in the receiver chamber 15, because of the interrupted comparison beam, so that the value 100 results for the difference signal DS. This is supposed to yield the calibration value 30 when weighted with the weighting factor K1=1 and the additional factor K2 to be determined, so that with the calculation 100·K1·K2=100·K2=30, the additional factor is calculated to be K2=0.3.

Operational analyses of measurement gas subsequently take place with the amplifier stage 23 bridged and the diaphragm 26 pushed out of the comparison beam path 5, where the difference signal DS obtained is weighted with the weighting factor K1 to generate the measurement value MW.

Due to contamination in the measurement cuvette 6, changes in the radiation source 1, or other interference influences, regular recalibration of the two-beam gas analyzer is required. This is done in such a manner that the measurement cuvette 6 is filled with inert gas 11. Although the inert gas 11 does not influence the radiation intensity, the radiation intensity in the measurement cuvette 6 is reduced by the interference influences which are present, so that a difference signal caused by the interference influences of DS ≠0 is obtained. This zero point deviation is at first compensated by automatic adjustment of the radiation source 1 or the beam splitter 2, or by adjusting the movable beam-limiting element 9 for beam limitation.

FIG. 4 shows that a difference signal DS with the value 20 is obtained in the measurement cuvette 6 filled with inert gas, proceeding from the numerical examples in FIG. 2 and 3, in case of an interference-influenced intensity reduction of 20%. As shown in FIG. 5, this zero point deviation is compensated by changing the beam intensity introduced into the measurement cuvette 6 and the comparison cuvette 13 to 111.11 and 88.89, respectively.

In a second step, the comparison beam path 5 is interrupted with the diaphragm 26, and, while the switch 24 is open, the weighting factor K1 is corrected in such a way that the measurement value MW corresponds to the calibration value again.

As FIG. 6 shows, the value 88.89 is obtained for the difference signal DS if the comparison beam 5 is interrupted. This is supposed to yield the measurement value MW=30 when weighted with the weighting factor K1, to be corrected, and the additional factor K2=0.3, so that with 88.89·K1·K21=88.89·K1·0.3=30, the new weighting factor K1=1.125 is obtained.

Subsequent to recalibration of the two-beam gas analyzer as just described, operational analyses of measurement gas 10 take place with the amplifier stage 23 bridged and the diaphragm 26 removed from the comparison beam path 5. The difference signal DS obtained is weighted with the corrected weighting factor K1.

FIG. 7 illustrates the foregoing using the example of a measurement gas which causes an intensity reduction of 40% in the measurement beam 4 in the measurement cuvette 6. Because of the additional interference-influenced intensity reduction of 20%, the intensity value 53.33 is received in the receiver chamber 14. The comparison beam 5 which enters the receiver chamber 15 has the intensity value 88.89, so that the difference signal DS=35.56 is obtained. From the difference signal DS, the correct measurement value MW=40 for the measurement gas to be analyzed is generated by weighting with the corrected weighting factor K1=1.125.

In the exemplary embodiment of the present invention described, compensation of interference-influenced zero point deviations take place by readjusting the radiation source 1 or the beam splitter 2 or by means of the movable beam-limiting element 9, as part of the recalibration. An alternative zero point equalization will be explained below which takes place exclusively within the framework of signal processing of the difference signal DS, so that the mechanical adjustment of elements of the two-beam gas analyzer is advantageously eliminated.

Proceeding from the example according to another embodiment of the present invention shown in FIG. 4, in which the difference signal DS=20 is obtained on the basis of an interference-influenced intensity reduction of 20% in the measurement cuvette 6 filled with inert gas, such zero point deviation is stored in memory as an offset value DS0 (FIG. 1) in the control device 27, when recalibrating the two-beam gas analyzer. To determine the corrected weighting factor K1, the comparison beam 5 is interrupted, in accordance with FIG. 8, so that the difference signal DS=80 is obtained. This is now supposed to yield the measurement value MW=30, when weighted with the weighting factor K1 to be corrected, and the additional factor K2=0.3, so that from 80·K1·K2=80·K1 ·0.3=30 the new weighting factor of K1=1.25 is obtained.

Subsequent to recalibration of the two-beam gas analyzer, operational analyses of measurement gas 10 again take place with the amplifier stage 23 bridged and with the diaphragm 26 removed from the comparison beam path 5. The difference signal DS obtained in this way is corrected with the offset value DS0 stored in memory in the control device 27, and subsequently weighted with the corrected weighting factor K1, to generate the measurement value MW.

FIG. 9 illustrates the above with the example of a measurement gas which causes an intensity reduction of 40% in the measurement beam 4 in the measurement cuvette 6. Because of the additional interference-influenced intensity reduction of 20%, the intensity value 48 is received in the receiver chamber 14. The comparison beam 5, which enters the receiver chamber 15 without attenuation, has the intensity value 100, so that the difference signal DS=52. This difference signal DS is corrected with the offset value DS0=20, and subsequently weighted with the corrected weighting factor K1=1.25, so that the correct measurement value MW=(DS−DS0)·K1=(52−20) 1.25=40 is obtained for the measurement gas to be analyzed.

The circuit blocks 21 . . . 24 and 27 shown in FIG. 1 are to be understood primarily as function blocks whose functions can be implemented both by a hardware circuit and by a program sequence in a processor. The adjustment of the radiation source 1, the beam splitter 2, or the movable beam-limiting element 9, as indicated with the double arrow 25, furthermore contains all the other possible measures which can contribute to an adjustment in distributing the radiation between the measurement cuvette 6 and the comparison cuvette 13. The difference signal DS generally describes the difference between the radiation exiting from the measurement cuvette 6 and the radiation exiting from the comparison cuvette 13, and can also be generated in different manner than with the pressure or flow detector 17 shown, for example with radiation-sensitive semiconductor detectors.

What is claimed:

1. A method for calibrating a two-beam gas analyzer, comprising the steps of:
   providing a measurement cuvette for passing a measurement beam therethrough to generate a measurement signal;
   filling a comparison cuvette with a comparison gas and passing a comparison beam therethrough to generate a comparison signal;
   generating, with a detector arrangement, a difference signal as a function of the measurement signal and the comparison signal, the detector arrangement following the measurement cuvette and the comparison cuvette;
   generating, with a signal processing device, a measurement value corresponding to a measurement gas concentration by weighting the difference signal with a weighting factor which is adjusted when the measurement cuvette is filled with a calibration gas so that the measurement value corresponds to a calibration value of the calibration gas;
   determining an additional factor when the comparison beam is intercepted and the measurement cuvette is not filled or is filled with an inert gas, wherein the additional factor is determined so that the difference signal corresponds to the calibration value when weighted with the weighting factor and the additional factor;
   determining a zero point deviation of the difference signal during subsequent calibration processes when the measurement cuvette is not filled or is filled with the inert gas; and
   correcting the weighting factor when the comparison beam is interrupted so that the difference signal corresponds to the calibration value when weighted with the corrected weighting factor and the additional factor.

2. The method according to claim 1, wherein the measurement cuvette is filled with a measurement gas.

3. The method according to claim 2, further comprising the step of:
   applying the zero point deviation to an additional difference signal obtained as an offset value when the measurement gas is analyzed.

4. The method according to claim 2, wherein the weighting of the difference signal with the weighting factor and the additional factor occurs in two subsequent amplifier stages each having adjustable amplification.

5. The method according to claim 4, wherein one of the two amplifier stages is bridged when the measurement gas is analyzed.

6. The method according to claim 1, further comprising the steps of:
   changing the comparison beam and the measurement beam to zero for reducing the zero point deviation; and
   correcting the weighting factor after changing the comparison and measurement beams.

7. The method according to claim 6, wherein the step of changing the comparison beam and the measurement beam includes inserting an element into a comparison beam path to limit the comparison beam.

8. The method according to claim 1, wherein the comparison beam is interrupted using a controllable diaphragm.

9. A two-beam gas analyzer comprising:
   a measurement cuvette through which a measurement beam is passed to generate a measurement signal;
   a comparison cuvette filled with a comparison gas and through which a comparison beam is passed to generate a comparison signal;
   a detector arrangement following the measurement cuvette and the comparison cuvette, the detector arrangement generating a difference signal as a function of the measurement and comparison signals;
   a signal processing device for generating a measurement value corresponding to a measurement gas concentration, the measurement value being generated by weighting the difference signal with an adjustable weighting factor;

a diaphragm which can be selectively inserted into the comparison beam;

a device which can be selectively inserted for weighting the difference signal with an adjustable additional factor; and two amplifier stages for comparing the difference signal with the weighting factor and the additional factor.

10. The two-beam gas analyzer according to claim 9, wherein the measurement cuvette is filled with a measurement gas.

11. The two-beam gas analyzer according to claim 9, wherein one of the two amplifier stages is bridged using a controllable switching device.

* * * * *